United States Patent [19]

Shibata

[11] Patent Number: 5,169,543
[45] Date of Patent: Dec. 8, 1992

[54] SERUM SEPARATION SEALANT AND FINE RESIN PARTICLES USING THE SAME

[75] Inventor: Toshiko Shibata, Tokyo, Japan

[73] Assignee: Nippon Paint Co., Ltd., Osaka, Japan

[21] Appl. No.: 499,752

[22] Filed: Mar. 27, 1990

Related U.S. Application Data

[63] Continuation-in-part of Ser. No. 384,365, Jul. 25, 1989, abandoned.

[30] Foreign Application Priority Data

Jul. 26, 1988 [JP] Japan .................. 63-184590
Jul. 26, 1989 [JP] Japan .................. 1-191540

[51] Int. Cl.$^5$ ............................. B01D 21/26
[52] U.S. Cl. ..................... 210/789; 210/516; 210/782; 210/787; 252/60; 422/101; 422/102; 436/177
[58] Field of Search ............ 436/177; 210/789, 516, 210/515, 782, 787; 252/60, 62.3 R, 62.3 Q; 422/102, 101

[56] References Cited

U.S. PATENT DOCUMENTS

| | | | |
|---|---|---|---|
| 3,780,935 | 12/1973 | Lukacs et al. | 494/37 |
| 3,852,194 | 12/1974 | Zyne, Jr. | 210/789 |
| 3,920,557 | 11/1975 | Ayres | 210/516 |
| 3,963,119 | 6/1976 | Lukacs et al. | 210/789 |
| 4,140,631 | 2/1979 | Okuda et al. | 210/789 |
| 4,180,465 | 12/1979 | Murty | 210/516 |
| 4,350,593 | 9/1982 | Kessler | 210/516 |
| 4,975,475 | 12/1990 | Tsuchiya et al. | 204/181.7 |

FOREIGN PATENT DOCUMENTS 0044822 1/1982 European Pat. Off. .
2264594 10/1975 France .
52-137181 11/1977 Japan .

Primary Examiner—Robert A. Dawson
Assistant Examiner—Sun Uk Kim
Attorney, Agent, or Firm—Sughrue, Mion, Zinn, Macpeak & Seas

[57] ABSTRACT

A serum separation sealant containing 0.1 to 20 parts by weight of fine resin particles having an average particle size of 0.01 to 2 μm and having an internal crosslinking density of 0.1 to 3 mmol/g and 100 parts by weight of a gelatinous material.

6 Claims, No Drawings

SERUM SEPARATION SEALANT AND FINE RESIN PARTICLES USING THE SAME

CROSS REFERENCE TO RELATED APPLICATION

This application is a continuation-in-part of Ser. No. 384,365, filed July 25, 1989 now abandoned.

BACKGROUND OF THE INVENTION

1 Field of the Invention

The present invention relates to a serum separation sealant for separating serum (or plasma) and blood clot (i.e., "sealant") by centrifugation of blood and to a fine resin particles used for the same.

2. Description of the Related Art

The analysis of the biochemical components of blood is essential in modern medical treatments, and serum separated from whole blood is widely used as the specimens for the analysis of the biochemical components.

Attempts have been made in, for example, U.S. Pat. No. 3,852,194, when centrifuging blood to separate the serum and blood clot, the desired serum is obtained by using a barrier between the two layers (i.e., serum and blood clot), and then decanting the serum without the use of a pipette. Such barriers may be classified as solid materials, liquid materials, or gelatinous (or gel-like) materials. Liquid materials and gelatinous materials are superior in separation performance and separation efficiency compared with solid materials and further are superior in terms of workability. Silicone resins, polyester resins, acrylic resins, and other liquid resins which have a suitable specific gravity and viscosity may be used as liquid materials. When desiring to impart structural viscosity to these liquid resins or when the resin does not have a suitable specific gravity and viscosity, silica, etc. may be dispersed in the liquid resin to form a gelatinous material. Examples of gelatinous or gel-like materials are disclosed in Japanese Unexamined Patent Publication (Kokai) No. 59-68672. When a blood collecting tube is filled in advance with said gelatinous material, it is preferable to use a material with a structural viscosity such that it will not flow in the distribution stage.

On the other hand, when separating the blood, it is necessary to apply as small a centrifugal force (for example, less than 1500G) as possible in a short time (for example, less than 10 minutes) so as to prevent and to suppress effects of hemolysis on the clinical examination values. To promote movement of the gelatinous materials and form a barrier under a low centrifugal force, it is preferable that the viscosity of the gelatinous materials be low. The barrier of the gelatinous material, formed under centrifugation, must be sturdy or firm to prevent breakdown during the decantation of the serum.

Thus, it is necessary that the gelatinous material possesses transport stability and partitioning ability and also exhibits excellent movability.

Japanese Unexamined Patent Publication (Kokai) No. 52-137181 discloses a blood collection tube in which plastic resin spheres having a size of 0.05 to 2.0 mm (e.g., polystyrene) are placed on a gelatinous material layer composed of liquid materials such as liquid polybutadiene and U.S. Pat. No. 3,920,557 discloses the use of beads as a solid barrier. However, these techniques still have problems with decantation and hemolysis.

SUMMARY OF THE INVENTION

Accordingly, the objects of the present invention are to eliminate the above-mentioned disadvantages of the prior art and to provide a sealant with the following properties:

(i) the ability to prevent the flow due to vibration or overturning in the distribution stage;

(ii) good partitioning ability between the serum and blood clot keeping the purity of separated serum, (iii) the suppression of outflow of blood clot and;

(iv) the improvement of the yield of serum even upon decantation immediately after separation.

Another object of the present invention is to provide a sealant and fine resin particles used for the same which achieve reliable movement under centrifugation by placing particulate material with a larger specific gravity than the sealant on the surface of the sealant dispensed.

Other objects and advantages of the present invention will be apparent from the following description.

In accordance with the present invention, there is provided a serum separation sealant (i.e., "sealant") comprising 0.1 to 20 parts by weight of fine resin particles having an average particle size of 0.01 to 2 $\mu$m and 100 parts by weight of a gelatinous material.

In accordance with the present invention, there is also provided resin particles usable for a sealant wherein the internal crosslinking density is 0.1 to 3 mili mol/g and the average particle size is 0.01 to 2 $\mu$m.

The term "gelatinous material" used herein means a gel-like material having a viscosity of 20 to 5000 poise (25° C.) and a specific gravity of 0.94 to 1.05 at 25° C. and comprising a liquid resin or a mixture thereof or a mixture of at least one liquid and at least one filler, preferably chemically stable for keeping the viscous state.

DESCRIPTION OF THE PREFERRED EMBODIMENTS

According to the present invention, as mentioned above, the intermixture of specific fine resin particles into a sealant enables the achievement of structural viscosity of the sealant in a short time. Therefore, after the sealant is dispensed in a serum separation tube, it is no longer necessary to allow the tube to stand vertically for a long time to prevent flow of the sealant as in the past, and it is possible to greatly shorten the time until transport is possible.

Further, it is possible to suppress flow due to vibration during distribution and thus facilitate handling. The barrier formed between the serum and blood clot (after centrifugation) is stable in the sealing and prevents migration of the red cell component to the serum. Thus, decantation for removal of the serum becomes possible in a shorter time than in the past. At this time, there is no occurrence of breakdown of the barrier and the serum can be separated at a high purity and yield.

Note that when the viscosity of the sealant is high, rather than raise the speed of centrifugation, use may be made of glass particulates, sand, etc. or plastic particulates having a specific gravity higher than the sealant and a diameter of 1 to 5 mm so as to make the sealant move up at a centrifugal force smaller than usual and thus enable more reliable formation of the barrier.

The particulate material is not particularly limited and it is sufficient if it is water repellant and inert with respect to blood. Sufficient amount of the particulate material is required in order to promote the movement of the sealant and form a reliable barrier.

As for the liquid resin used in the present sealant different resins can be applied such as silicone resin as disclosed in U.S. Pat. No. 3,852,194, acrylic resin as disclosed in Japanese Unexamined Patent Publication (Kokai) No. 59-68672, polyester resin as disclosed in U.S. Pat. No. 4,101,422, polybutadiene resin, and other resins. These liquid resins may be used alone or adjusted in specific gravity and viscosity with a specific gravity and viscosity adjusting agent.

Examples of a filler usable for the adjustment of the specific gravity and/or viscosity are silica, barium sulfate, alumina, calcium carbonate, talc, bentonite, and organic gelation agents (e.g., condensates of higher polyhydric alcohols with benzaldehyde).

The fine resin particles usable in the present invention have an average particle size of 0.01 to 2 $\mu$m, crosslinked to a degree, making them insoluble by the above-mentioned resin liquid or gelatinous composition. If the average particle size is over 2 $\mu$m, lumps easily forms in the sealant and if less than 0.01 $\mu$m, the structural viscosity effect cannot be sufficiently obtained. The crosslinking density is preferably 0.1 to 3 mili mol/g. When the crosslinking density is more than 3 mili mol/g, the sealant is too hard and a suitable viscosity characteristic cannot be obtained. When the crosslinking density is less than 0.1 mili mol/g, there occurs swelling by the liquid resin.

As for synthesis of such fine resin particles, in the prior art, an ethylenically unsaturated monomers is subjected to emulsion polymerization with a crosslinkable copolymer in an aqueous medium to make a particulate polymer and finally the water is removed by solvent substitution, azeotropic distillation, centrifugation, filtration, drying, etc.; the process for fine resin particles wherein (i) an ethylenically unsaturated monomer and crosslinking polymerizing monomer are copolymerized in the presence of a stabilizing agent in a nonaqueous organic solvent which dissolves the monomer but does not dissolve the polymer, and (ii) a dispersion of a particulate copolymer, is obtained by condensation reaction known as the NAD process; and the process wherein synthetic resin obtained by solvent polymerization or bulk polymerization is subjected to another emulsion process and internal crosslinking reaction process to make fine resin particles.

The fine resin particles usable in the present invention are not limited to those obtained by any specific production process so long as the above-mentioned requirements are met. Examples of fine resin particles are those obtained from one or more types of reactive monomers or reactive macromers, such as acrylic resin, polyester resin, epoxy resin, aminoplast resin, urethane resin, imide resin, silicone resin, olefine resin, and diene resin. The resin usable in the present invention is not limited to any specific type.

The above-mentioned sealant according to the present invention may be used in various ways to separate blood by centrifugation. For example, (a) a method of previously dispensing the sealant in a blood collection tube, followed by collecting blood thereinto; (b) a method of collecting blood into a blood collection tube, followed by dispensing the sealant; (c) a method of collecting blood into a blood collection tube, followed by using a dispenser shaped such that the dispenser can be placed on top of the blood collection tube and that the sealant flows out when a centrifugal force is applied; and (d) a method of dispensing the sealant in a blood collection tube, and evacuating the tube followed by collecting blood and centrifuging.

EXAMPLES

Examples of the present invention will be explained below, but the technical scope of the present invention is not intended to be limited by these Examples. In the following Examples, "parts" and "%" indicate parts or percent by weight unless otherwise indicated.

PREPARATION EXAMPLE 1

A one-liter reaction vessel provided with a stirrer, cooler, and temperature controller was charged with 282 parts of deionized water, 10 parts of polyester resin having amphoteric ion groups and 0.75 parts of dimethylethanol amine. The mixture was stirred while holding the temperature at 80° C. to dissolve the components. To the solution, a solution containing 4.5 parts of azobiscyanovaleric acid dissolved in 45 parts of deionized water and 4.3 parts of dimethylethanolamine was added. Next, a mixed solution containing 70.7 parts of methylmethacrylate, 30 parts of 2-hydroxyethylacrylate, and 4.5 parts of ethylene glycol dimethacrylate was dropwise added for 60 minutes. After the end of the dropwise addition, further a solution of 1.5 parts of azobiscyanovaleric acid dissolved in 15 parts of deionized water and 1.4 parts of dimethylethanolamine was added thereto. Stirring was continued at 80° C. for 60 minutes. As a result an emulsion with 45 percent of nonvolatile components, a pH of 7.2, a viscosity of 92 cps (25° C.) and an average particle size of 0.156 $\mu$m was obtained. This emulsion was spray dried to obtain the resin particles (I). The crosslinking density was 1.01 mmol/g.

PREPARATION EXAMPLE 2

A flask equipped with a stirrer and a thermometer was charged with 200 parts of deionized water. To this were added 6 parts of sodium dodecylbenzenesulfonate and 4 parts of polyvinyl alcohol and these dissolved therein. Further, 70 parts of long oil alkyd and 2 parts of cobalt naphthenate were added and emulsified to obtain an average particle size of 0.2 $\mu$m. Further, air was blown into this and at the same time the temperature was held at 80° C. for 8 hours to thereby obtain the fine resin particles. The dispersion containing fine resin particles (II) was spray dried. The crosslinking degree of the resin particles obtained was 2.05 mmol/g.

EXAMPLE 1

A mixture of 2-ethylhexylacrylate, n-butylacrylate, and t-butylperoxy 2-ethylhexanoate was dropped into warm xylene to obtain a polymer solution. The solvent was removed from this under vacuum and heating to obtain a liquefied resin having a specific gravity of 1.029 and a viscosity of 440PS.

Into 100 parts of this liquid resin was dispersed 3.2 parts of silicon dioxide (Degussa, Aerosil ® R972, specific gravity 2.2). Into this was dispersed 1.3 parts of the fine resin particle obtained in Manufacturing preparation Example 2 to obtain a sealant with a viscosity of 2100PS/1 sec$^{-1}$/25° C. and a specific gravity of 1.045. The sealant obtained here was filled in an amount of 1.3 grams into the bottom of a glass test tube having an inside diameter of 13 mm and a length of 100 mm. This was held vertically at 20° C., after five minutes and 60 minutes was turned horizontally, then after one day the flow distance of the sealant was determined.

Further, 8 ml of fresh human blood was dispensed in the sealant-filled test tube and left to stand for one hour at room temperature, then centrifuged at 1000G and 1500G for 10 minutes each. The performance of the barrier formed was then examined.

EXAMPLE 2

A mixture of ethylacrylate, laurylmethacrylate, and t-butylperoxy 2-ethylhexanoate was dropped into warm xylene to obtain a polymer solution. The solvent was removed from this under vacuum and heating to obtain a liquid resin having a specific gravity of 1.001 and a viscosity of 230PS. Into 100 parts of this resin were dispersed 4.5 parts of silicon dioxide (Aerosil ®R972) and 4.0 parts of the silicone dioxide (Nippon Aerosil, Aerosil ®200). Into this was dispersed 0.8 part of the fine resin particle obtained in Manufacturing Example 1 to obtain a sealant with a viscosity of 1950PS/1 sec$^{-1}$/25° C. and a specific gravity of 1.046. The flow of the sealant and the ability to form a barrier were examined in the same way as in Example 1.

EXAMPLE 3

Neopentylglycol and 1,2-propanediol were reacted with azelaic acid and dimer acid to obtain a liquid resin having a viscosity of 210PS and a specific gravity of 1.026. To this were added 2 parts of silicon dioxide (Aerosil ®R972) and 1.5 parts of silicone dioxide (Aerosil ®200) to obtain a dispersion. Into this was dispersed 1.5 parts of preparation the fine resin particle obtained in Manufacturing Example 2 to obtain a sealant with a viscosity of 2000PS/1 sec$^{-1}$/25° C. and a specific gravity of 1.044.

The flow of the sealant and the ability to form the barrier were examined in the same way as in Example 1.

EXAMPLE 4

The same procedure was followed as in Example 1 except that 8 ml of fresh human blood was collected into a vacuum blood collection tube. The results are shown in Table 2.

EXAMPLE 5

The sealant obtained in Example 1 was dispensed into the bottom of a blood collection tube, then five to six soda glass beads of a specific gravity of 2.5 and an average bead size of 1.6 to 2.0 mm were placed on the surface of the sealant. Into this, 8 ml of fresh human blood was collected and centrifugation was performed in the same way as in Example 1.

EXAMPLE 6

The sealant obtained in Example 2 was dispensed into the blood collection tube, then 1 bead of a specific gravity of 2.8 and a bead size of 5 mm was placed on the surface of the sealant. Into this, 8 ml of fresh blood was collected and centrifugation was performed in the same way as in Example 1. The flow and partitioning performance of the sealant were evaluated.

COMPARATIVE EXAMPLE 1

The same procedure was followed as in Example 1 to obtain a sealant, except that no fine resin particles were used. The flow and barrier separating performance of the sealant were evaluated as in Example 1.

COMPARATIVE EXAMPLE 2

The same procedure was followed as in Example 2 to obtain a sealant, except that no fine resin particles were used at all. The flow and barrier separator performance of the sealant were evaluated as in Example 1.

COMPARATIVE EXAMPLE 3

The same procedure was followed as in Example 2 to obtain a sealant having a specific density of 1.045, except that 100 parts of polystyrene sphere having a specific density of 1.043 and an average particle size of 0.05 mm was used instead of dispensing the fine resin particle.

The flow and barrier separating performance of the sealant were evaluated as in Example 1.

The results of Examples 1 to 6 and Comparative Examples 1 to 3 are shown in Table 1.

TABLE 1

| No. | | Flow After 5 min (mm) | Flow After 60 min (mm) | Barrier formation 1000 G 10 min (%) | 1500 G 10 min (%) | Sealing Property | Degree of intermixture of red cell |
|---|---|---|---|---|---|---|---|
| Example | 1 | 3 | 0.5 | 60 | 90 | ++ | None |
|  | 2 | 1.5 | 0 | 60 | 90 | +++ | None |
|  | 3 | 4 | 0.5 | 70 | 100 | ++ | None |
|  | 4 | 4 | 0.5 | 100 | 100 | +++ | None |
|  | 5 | — | — | 100 | 100 | +++ | None |
|  | 6 | — | — | 100 | 100 | +++ | None |
| Comparative Example | 1 | 29 | 14 | 90 | 100 | ± | Slight |
|  | 2 | 26 | 12 | 80 | 100 | ± | Slight |
|  | 3 | 16 | 9 | 100 | 100 | + | Hemolysis |

*Evaluation criteria (at a force of 1500 k × 10 min.)
+++ Excellent
++ Somewhat good
+ Somewhat poor
± Poor

EXAMPLE 7

An 8 ml amount of fresh human blood was dispensed in a blood collection tube, followed by allowing to stand at room temperature for one hour. Then, 1.3 g of the sealant obtained in Example 2 was dispensed through a dispensing machine in the blood collection tube and the centrifugal separation was carried out. Separation performance was evaluated in the same manner as in Example 1. The results are shown in Table 2.

EXAMPLE 8

The sealant obtained in Example 2 was put in a dispenser which fitted on the top of the blood collection tube and having a nozzle in the lower portion thereof. More specifically, the dispenser was in the reverse conical form and filled with sealant inside. The dispenser opened at the maximum circular section to the opening portion of the blood collection tube and had a bottom nozzle with a diameter of 1.5 mm. When centrifuged, the sealant flew through the nozzle.

An 8 ml amount of fresh human blood was collected in the blood collection tube, followed by allowing to stand at room temperature for one hour. Then, on the top of this blood collection tube, a dispenser having the sealant of Example 2 filled therein was placed and followed by the centrifugal separation. Evaluation of the formed barrier was determined in the same manner as in Example 1. The results are shown in Table 2.

COMPARATIVE EXAMPLE 4

The sealant obtained in Comparative Example 3 was filled in a dispenser. The dispenser was placed on the open end of a blood collecting tube, in which 8 ml of fresh human blood was collected, followed by centrifugation. The results are shown in Table 2.

COMPARATIVE EXAMPLE 5

The same procedure was followed as in Example 6 except that the sealant of Comparative Example 1 was used. The results are shown in Table 2.

COMPARATIVE EXAMPLE 6

The same procedure was followed as in Example 7, except that the sealant of Comparative Example 1 was used. The results are shown in Table 2.

In Examples 7 and 8 and Comparative Examples 4 to 6, the drip from the nozzle of the dispenser after separation was evaluated.

TABLE 2

| No. | | Drip from nozzle | Sealing property | Degree of intermixture of red cell |
|---|---|---|---|---|
| Example | 7 | No | +++ | None |
|  | 8 | No | +++ | Slight |
| Comparative Example | 4 | Slight | ± | Hemolysis |
|  | 5 | Slight | ± | Slight |
|  | 6 | Slight | ± | Hemolysis |

EXAMPLES 9 AND 10 AND COMPARATIVE EXAMPLE 7

The following materials were used for preparing sealants used in Examples 9 and 10 and Comparative Example 7.

Silicon fluid: Silicone medical fluid 360 having a specific gravity of 0.974 (25°) and a viscosity of 8 ps/1 sec$^{-1}$/25° C. (Dow Corning)

Silicon dioxide: Aerosil R 972 (Degussa); Aerosil 200 (Degussa)

Resin particle: Resin prepared in the Preparation Example 1

The geletinous materials having the following compositions were prepared in the same manner as mentioned above.

| Material | Comparative Example 7 | Example 9 (parts) | Example 10 |
|---|---|---|---|
| Silicon fluid 360 | 100 | 100 | 100 |
| Aerosil R 972 | 13 | 12.5 | 13 |
| Aerosil 200 | 2 | 2 | 2 |
| Resin Particle of Preparation Example 1 | — | 0.5 | 2 |

The properties and performance of the sealants obtained above were evaluated in the same way as mentioned above. The results are shown in Table 3.

TABLE 3

| Items | Comparative Example 7 | Example 9 | Example 10 |
|---|---|---|---|
| Viscosity (Poise/1 sec$^{-1}$/25° C.) | 1360 | 1570 | 1710 |
| Yield value (dyne/cm$^2$) | 1018 | 457 | 516 |
| Specific gravity | 1.049 | 1.047 | 1.050 |
| Movement of gel (1300 G × 10 min.) | x*[1] | ○ | ○ |
| Viscosity after aging*[2] (poise/1 sec$^{-1}$/25° C.) | | | |
| after 1 week | 960 | 1600 | 1790 |
| after 1 month | 640 | 1600 | 1800 |

*[1] Energizer has to be applied for getting gel barrier
*[2] Aging condition: Room temperature As is clear from the results shown in Table 3, when the viscosity was adjusted with the silicon dioxide without using the liquid resin as in Comparative Example 7, the yield value was unpreferably high and the resultant gel was not moved, unless an energizer was used, and therefore, the resultant gel-like material did not form a barrier between the serum and the blood clot. Contrary to this, according to the present invention, since the resin was used, the barrier was advantageously formed between the serum and the blood clot.

EXAMPLE 11 AND COMPARATIVE EXAMPLES 8 AND 9

The following gelatinous materials having the following compositions were prepared in the manner as mentioned above.

| Material | Example 11 | Comparative Example 8 (parts) | Comparative Example 9 |
|---|---|---|---|
| Acryl polymer of Example 2 | 100 | 100 | 100 |
| Aerosil R 972 | 4.5 | 4.5 | 5.3 |
| Aerosil 200 | 4.0 | 4.0 | 4.0 |
| Resin particle of Preparation Example 1 | 0.8 | — | — |

The evaluation results are shown in Table 4.

TABLE 4

| Items | Example 11 | Comparative Example 8 | Comparative Example 9 |
|---|---|---|---|
| Viscosity (Poise/1 sec$^{-1}$/25° C.) | 1950 | 720 | 800 |
| Yield value (dyne/cm$^2$) | 182 | 39 | 45 |
| Specific gravity | 1.045 | 1.046 | 1.050 |

TABLE 4-continued

| Items | Example 11 | Comparative Example 8 | Comparative Example 9 |
|---|---|---|---|
| Flow after 5 minutes (mm) | 1.5 | 26 | 21 |
| Barrier (1300 G × 10 mm) (%) | 100 | 100 | 100 |
| Sealing property | +++ | ± | ± |

I claim:

1. A serum separation sealant consisting essentially of 0.1 to 20 parts by weight of the fine resin particles having an average particle size of 0.01 to 2 μm and having an internal crosslinking density of 0.1 to 3 mmol/g and 100 parts by weight of a gelatinous material.

2. A blood collection tube for serum separation comprising a sealant consisting essentially of 0.1 to 20 parts by weight of the fine resin particles having an average particle size of 0.01 to 2 μm and having an internal crosslinking density of 0.1 to 3 mmol/g and 100 parts by weight of a gelatinous material is placed.

3. A blood collection tube as claimed in claim 2, wherein the blood collection tube is under vacuum.

4. A method of separating blood comprising the steps of:
   (i) placing a sealant consisting essentially of 0.1 to 20 parts by weight of fine resin particles having an average particle size of 0.01 to 2 μm and having an internal crosslinking density of 0.01 to 3 mmol/g and 100 parts by weight of a gelatinous material in a blood collection tube;
   (ii) placing blood to be separated in the blood collection tube; and
   (iii) effecting a centrifugal separation.

5. A method of separating blood comprising the steps of:
   (i) placing blood to be separated in a blood collection tube;
   (ii) placing a sealant consisting essentially of 0.1 to 20 parts by weight of fine resin particles having an average particle size of 0.01 to 2 μm and having an internal crosslinking density of 0.1 to 3 mmol/g and 100 parts by weight of a gelatinous material in the blood collection tube; and
   (iii) effecting a centrifugal separation.

6. A method of separating blood comprising the steps of:
   (i) placing blood to be separated in a blood collection tube;
   (ii) packing a sealant consisting essentially of 0.01 to 20 parts by weight of fine resin particles having an average particle size of 0.01 to 2 μm and having an internal crosslinking density of 0.01 to 3 mmol and 100 parts by weight of a gelatinous material, in a dispenser capable of moving the sealant down by centrifugal force;
   (iii) placing the dispenser on the top of the blood collection tube; and
   (iv) effecting the centrifugal separation.

* * * * *